(12) United States Patent
Rubbert (10) Patent No.: US 6,359,680 B1
(45) Date of Patent: *Mar. 19, 2002

(54) THREE-DIMENSIONAL OBJECT MEASUREMENT PROCESS AND DEVICE

(75) Inventor: Rudger Rubbert, Berlin (DE)

(73) Assignee: OraMetrix, Inc., Dallas, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,843

(22) PCT Filed: Aug. 19, 1997

(86) PCT No.: PCT/DE97/01797

§ 371 Date: Mar. 11, 1999

§ 102(e) Date: Mar. 11, 1999

(87) PCT Pub. No.: WO98/11403

PCT Pub. Date: Mar. 19, 1998

(30) Foreign Application Priority Data

Sep. 13, 1996 (DE) .......................................... 196 38 758

(51) Int. Cl.[7] .......................... G01C 3/00; G01B 11/24; G01B 3/22; G06K 9/00
(52) U.S. Cl. ...................... 356/3.06; 356/376; 382/154; 702/167
(58) Field of Search .......................... 382/154; 356/376, 356/3.06, 3.07; 702/167, 168

(56) References Cited

U.S. PATENT DOCUMENTS

| 4,567,347 A | * | 1/1986 | Ito et al. ...................... 356/376 |
| 4,634,278 A | | 1/1987 | Ross et al. .................... 356/376 |
| 5,085,502 A | * | 2/1992 | Womack et al. ............. 356/376 |
| 5,289,264 A | * | 2/1994 | Steinbichler ................. 356/376 |
| 5,309,243 A | | 5/1994 | Tsai |
| 5,372,502 A | | 12/1994 | Massen et al. |
| 5,545,039 A | * | 8/1996 | Mushabac .................... 433/215 |
| 5,604,817 A | | 2/1997 | Massen et al. .............. 382/120 |
| 5,608,211 A | | 3/1997 | Hirono et al. |

FOREIGN PATENT DOCUMENTS

| CA | 2163934 | 5/1996 |
| DE | 44 45 552 | 6/1995 |

OTHER PUBLICATIONS

Charles A. Pelizzari et al., "Accurate Three–Dimensional Registration of CT, PET, and/or MR Images of the Brain", *Journal of Computer Assisted Tomography*, 13(1):20–26, Jan./Feb., 1989.

Klaus D. Toennies et al, "Registration of 3D Objects and Surfaces", *IEEE Computer Graphics & Applications*, 1990, pp. 52–62.

Behrooz Kamgar–Parsi et al., "Registration of Multiple Overlapping Range Images: Scenes without Distinctive Features", *IEEE Transactions on Pattern Analysis and Machine Intelligence*, vol. 13, No. 9, Sep. 1991, pp. 857–871.

Hui Li et al., "Registration of 3–D Multimodality Brain Images by Curve Matching", *IEEE*, 1994, pp. 1744–1748.

Jean–Francois Mangin et al., "Nonsupervised 3D Registration of PET and MRI Data Using Chamfer Matching", *IEEE*, 1993, pp. 1262–1264.

* cited by examiner

Primary Examiner—Stephen C. Buczinski
(74) Attorney, Agent, or Firm—McDonnell Boehnen Hulbert & Berghoff (57) ABSTRACT

A three-dimensional object measurement process and device are disclosed by means of optical image capture, projection of patterns and triangulation calculations. The pattern projection unit and the image capture unit are separately designed and can be independently positioned and guided during the measurement process. This is particularly advantageous for diagnosis, therapy and documentation in the field of invasive medicine.

29 Claims, 4 Drawing Sheets

THREE-DIMENSIONAL OBJECT MEASUREMENT PROCESS AND DEVICE

The invention concerns a process for the three-dimensional measurement of objects through optical exposures, projected patterns, and calculations of triangulation, in which the devices for the projection of the pattern and for the image capture are constructed separately from one another and can, for the measurement, be positioned independently of one another.

Furthermore, the invention concerns a device for such a process.

The use of processes that work on an optical basis offer a multiplicity of advantages for the purpose of measuring. A measurement can be carried out quickly and without contact. Electronic image converters, such as CCD arrays, for example, the output signals of which can be stored or evaluated after digitalization, already belong to the state of the art.

Processes and devices for the representation and three-dimensional optical measurement of spatial surfaces are already known. These are based upon triangulation processes in which patterns of points, lines, or any other chosen patterns are projected, at a certain angle, onto the surface under consideration, and the projected patterns are captured, under another viewing angle, by means of an optical device and an image converter. The known geometry between the direction of projection and the direction of capture permits the three-dimensional calculation of support points of the surface.

If a uniform pattern of lines is projected onto an object with spatial extensions, for example, then, because of the surface shape of the object, a distorted line pattern is brought about in a direction of view which is different from the direction of projection. If the object is represented from this direction of consideration on a CCD-array by means of a suitable optical device, and the image signals are digitalized and made available to a data processing unit, then it is possible to identify the lines at the various points of the image and, given a knowledge of the optical path of the rays, and under consideration to the geometrical configuration of the projected pattern of lines, to compute the 3D coordinates by means of triangulation.

In the capture of several individual images with different directions of capture, it is already state of the art to combine the partial information obtained about three-dimensional surfaces by means of the 3D coordinates of corresponding surface segments into a total information by means of so-called "registration-algorithms".

It is now desirable to do the following for endoscopic investigations, for example:
  a) To use a separate unit for the projection of the pattern and for the capture of the image, and to use this with an orientation that is freely selectable in relation to the surface to be measured. In order to obtain relevant data for the calculation of the triangulation, a minimum angle between the orientation of both of the units should not be fallen short of in this connection;
  b) Insofar as a series of individual images is captured during the capture process, to change the position and orientation of both of the units independently of one another in relation to the object, such as for the simplification of the handling, for example, in order to be able to measure additional surface areas by means of additional image captures.

It is thus the task of the invention to create the process and the device for the three-dimensional measurement of objects of the type just described, in which the position and orientation of the image capture unit and of the projection unit can be adjusted to one another and, in the event that more than one capture is useful for this purpose, to follow the independent movement of the two units towards one another that has taken place during the course of the capture process. The geometrical connection between the image capture and the pattern projection determined for the specific individual image must then be taken into consideration for the calculation of triangulation.

This task is solved, in accordance with the invention, through the fact that:
  a) Through the use of an electronic surface image converter, a capture process is carried out;
  b) Through the use of a source of beams and suitable optical devices, a pattern is projected onto the object at an angle which is different from the direction of capture that is to be measured;
  c) Through the use of a suitable unit, the output signals of the image converter are digitalized, and these data are made available to a data processing apparatus;
  d) Through the use of a data processing apparatus, 3D coordinates of the points of the surface of the object to be measured are determined, by means of suitable circuits and/or algorithms, through calculations of triangulation from the image data of the individual images;

while additional devices are provided in such a manner, and/or the process coming for use and/or the devices are configured in such a manner, that the position and the orientation of the image capture unit and of the projection unit to one another can be determined. If the position and the orientation of both units to one another is known, then, for the capture of an individual image, 3D coordinates can be determined by means of a triangulation calculation, in the known manner and method, for a number of points of the surface.

It is, in accordance with the invention, advantageous to use additional devices for this purpose in order to measure the position and the orientation of the image capture unit and of the projection unit to one another.

In accordance with the invention, this can be carried out, in an advantageous manner, both directly as well as indirectly, both by means of scanning or in connection with measuring means, as well as without contact, such as by optical means, for example.

If information on the object which is additional to that information acquired from an individual exposure is now to be determined, then the image capture unit must be able to record a sequence of individual images. For the task in accordance with the invention, namely, that the projection unit and the image capture unit are moved differently during the course of the image capture process, the devices and/or processes in accordance with the invention must, in an advantageous manner, be configured in such a manner that the geometrical configuration of the image capture unit and of projection unit can be adjusted to one another for the sequential images.

This can, in accordance with the invention, be advantageously guaranteed through the fact that the above-stated measuring devices are also evaluated at the point in time of the exposures that are additionally carried out, and the measuring results are taken into consideration, in the way and manner described above, in the calculation of triangulation.

For the event that, in the sequence of the individual images, the object is recorded in such a manner that the 3D coordinates determined from the individual images describe surface segments that are in agreement to a considerable degree, then—as has been described above—the specific 3D information can be combined by means of "registration algorithms" corresponding to the state of the art.

If the capture of the individual images takes place in rapid sequence, then, with a corresponding handling of the units, it can be assumed that—first of all—the portion of corresponding surface segments is sufficient and—secondly—that the geometrical correspondence of the image capture unit and of the projection unit to one another has only been altered in extent in relation to the previous capture.

If, therefore, the coordination of both units in the first capture was known, for example, and if a considerable number of 3D coordinates describing the surface could be computed, then the information contained in the next capture differs in the following components:

a) The 3D coordinates of the corresponding surface segments can be represented displaced linearly in the three spatial directions;

b) The 3D coordinates of the corresponding surface segments can be represented displaced in a rotational manner in relation to the three spatial directions;

c) The relative position of the image capture unit and of the projection unit to one another can be changed linearly in the three spatial directions;

d) The relative position of the image capture unit and of the projection unit to one another can be changed in a rotational manner in relation to the three spatial directions.

For the purpose of the generalization of expressions, these possibilities of change will also be termed in the following as "degrees of freedom".

Matching algorithms—which form, from the different data records of 3D coordinates, the intersections of that data which are to be assigned to corresponding surface segments, and which vary and optimize the possible changes (a) and (b) listed above in such a manner that the intersection of the specific 3D data of both data records fit optimally with one another in regard to the corresponding displacements and rotations—already belong to the state of the art in the technical area of graphic data processing. One presupposition for this is that the changes (c) and (d) listed above are known.

Algorithms which systematically vary a finite number of degrees of freedom and optimize these in accordance with one or more criteria of quality are already known from numerical mathematics. In a systematic variation, however, the computational expense is raised to a higher power with every additional level of freedom.

Recursively gradated processes which, through a stochastic variation of the degree of freedom and a step-wise selection of each specifically best variant, under the assumption that the quantities of information that are to be evaluated are essentially similar, reach an optimal solution surprisingly quickly, are already known, in connection with the phrase "evolution strategies", from the field of bionics.

In this sense, it is, in accordance with the invention, advantageous for the solution of the task in accordance with the invention to use expanded matching algorithms in such a manner that:

First of all—In a recursive numerical process, multiple so-called "successor" variants are first formed through the stochastic variation of the above-stated degrees of freedom (c) and (d);

Secondly—For every successor variant, the 3D data records are, in the known manner, computed from image information by means of triangulation, in accordance with the assumptions made for the degrees of freedom (c) and (d);

Thirdly—For every successor variant, the intersections of those data which are to be assigned to the corresponding surface segments are formed, in the known way and manner, in a matching computation from the different data records of 3D coordinates, and the above-listed degrees of freedom (a) and (b) are varied and optimized in such a manner that the intersections formed from the specific 3D data of both data records can, under consideration of the specifically-selected geometrical change, be optimally transformed into one another in relation to the level of freedom (a) and (b);

Fourthly—Out of all of the successor variants, that one which has the maximum value achieved in regard to the agreement of the data from both data records describing the same surface segment is selected in the sense of an evolution;

Fifthly—Corresponding to the evolution strategy described, and proceeding from the assumptions that were made for the degrees of freedom (c) and (d) of the previously-selected best successor variants with reduced boundaries of the degrees of freedom (c) and (d), new successors of the next generation are again stochastically varied in different variants and, in a manner corresponding to the above-stated five points—first to fifth—it is then proceeded in a recursive manner for long enough until the boundaries of variation of the degrees of freedom (c) and (d), and the differences between the generations in regard to the maximum value achieved in every passage, are sufficiently small.

As the result, all information required is known with sufficient precision.

It is, in accordance with the invention, advantageous to construct the devices for the projection of the pattern and for the capture of the image in such a manner that these are connected rigidly and in an unambiguous position and orientation with one another during the capture of the first individual image. During the further course of the capture, the connection is detached and a movement independent of one another is thereby made possible. The additional three-dimensional measurement values of the object can then be computed, for every new image capture, with the expanded registration algorithm described above and, as described above, combined into a total information.

In an alternative manner, it is, in accordance with the invention, advantageous to measure the geometrical relation of the projection unit and of the image capture unit to one another through the fact that the pattern used is projected both onto the object as well as onto the image capture unit, and the pattern resulting on a defined surface rigidly connected with the image capture unit is recorded by one area of the image converter. In this sense, the image converter can record the object with one part of its areal field of view, and record the pattern projected onto the image capture unit with the other part.

In the evaluation of the image information, the geometrical position of the two units to one another is, in accordance with the invention, first of all advantageously computed from the distortion of the sample projected onto the surface of the image capture unit, which is, for example, flat and constructed as ground glass disk, by means of triangulation, and the object is, in addition, spatially measured, in relation to the assignment of both of the units to one another, in the way and manner as described above.

A process in which, in order to prevent multiplicities in the calculations of triangulation, coded patterns are projected onto the object, is already known from the German patent application "A process for increasing the significance of the three-dimensional measurement of objects" of the date Sep. 12, 1996 by the same applicant.

It is, in accordance with the invention, particularly advantageous to use coded patterns for the determination of the coordination of the projection unit and of the image capture unit to one another in such a manner.

A process and a device in which beam paths can be effectively or ineffectively switched in an alternating manner by means of optical means placed synchronously with the alternating image current of the image converter are already known from the German patent application number 196 36 354.3 by the same applicant.

It is, in accordance with the invention, particularly advantageous to synchronously switch the direction of view of the image capture unit, such as by means of two surface-active LCD-units—which are positioned on two optical axes of a beam splitting devices, for example—with the image alternating frequency of the image converter in such a manner that they are alternately optically permeable and non-permeable. This has the advantage that, for the purpose of determining the geometrical coordination of the projection unit with the image capture unit, the field of view of the image converter, and thereby the resolution in the representation of the object, does not have to be reduced.

It is, in accordance with the invention, advantageous to additionally provide further optical devices for the projection of a pattern which is different, for example, onto the image capture unit on the projection unit.

In an alternative manner to the surface rigidly connected with the image capture unit that has been described above, the pattern can, in accordance with the invention, be advantageously projected onto a separately-positioned surface with a known spatial extension, in order to determine the coordination of the image capture unit and of the projection unit with one another, and can be represented on the image converter of the image capture unit.

A second image capture unit for the purpose of determining the coordination of the image capture unit and of the projection unit with one another can advantageously be provided in accordance with the invention.

All of the configurations of the process and of the device that are described in this invention can, in a particularly advantageous manner, be combined with one another in multiple ways and manners in accordance with the invention.

The device for the three-dimensional measurement of objects of the type described above solves the task in accordance with the invention through the characteristics that:
  a) At least one electronic surface image converter which uses an optical device suitable for the capture of images is used;
  b) At least one device which carries out the digitalization of the output signals of the at least one image converter and makes these data available to a data processing apparatus is used;
  c) At least one device which permits the projection of a pattern is used;
  d) The devices for the projection of the pattern and for the capture of the image are constructed independently of one another;
  e) At least one data processing apparatus which uses suitable circuits and/or algorithms is suited for the calculation of 3D coordinates in accordance with the triangulation process; and:
  f) At least one device is suited for the determination of the geometrical coordination between the projection unit and the image capture unit.

In one configuration of the device in accordance with the invention which is particularly advantageous, the image capture unit is suitable for the capture of at least two successively following images.

One configuration of the device in accordance with the invention which is particularly advantageous provides devices which can store the data of at least two individual images.

One configuration of the device in accordance with the invention which is particularly advantageous provides devices which process the data of at least two individual images, and are able to combine these by means of suitable circuits and/or algorithms.

Further advantages, characteristics, and possibilities of application of the present invention result from the following description of preferred examples of implementation in connection with the attached diagrams, FIGS. 1, 2, 3 and 4. These depict the following.

Figure 1:
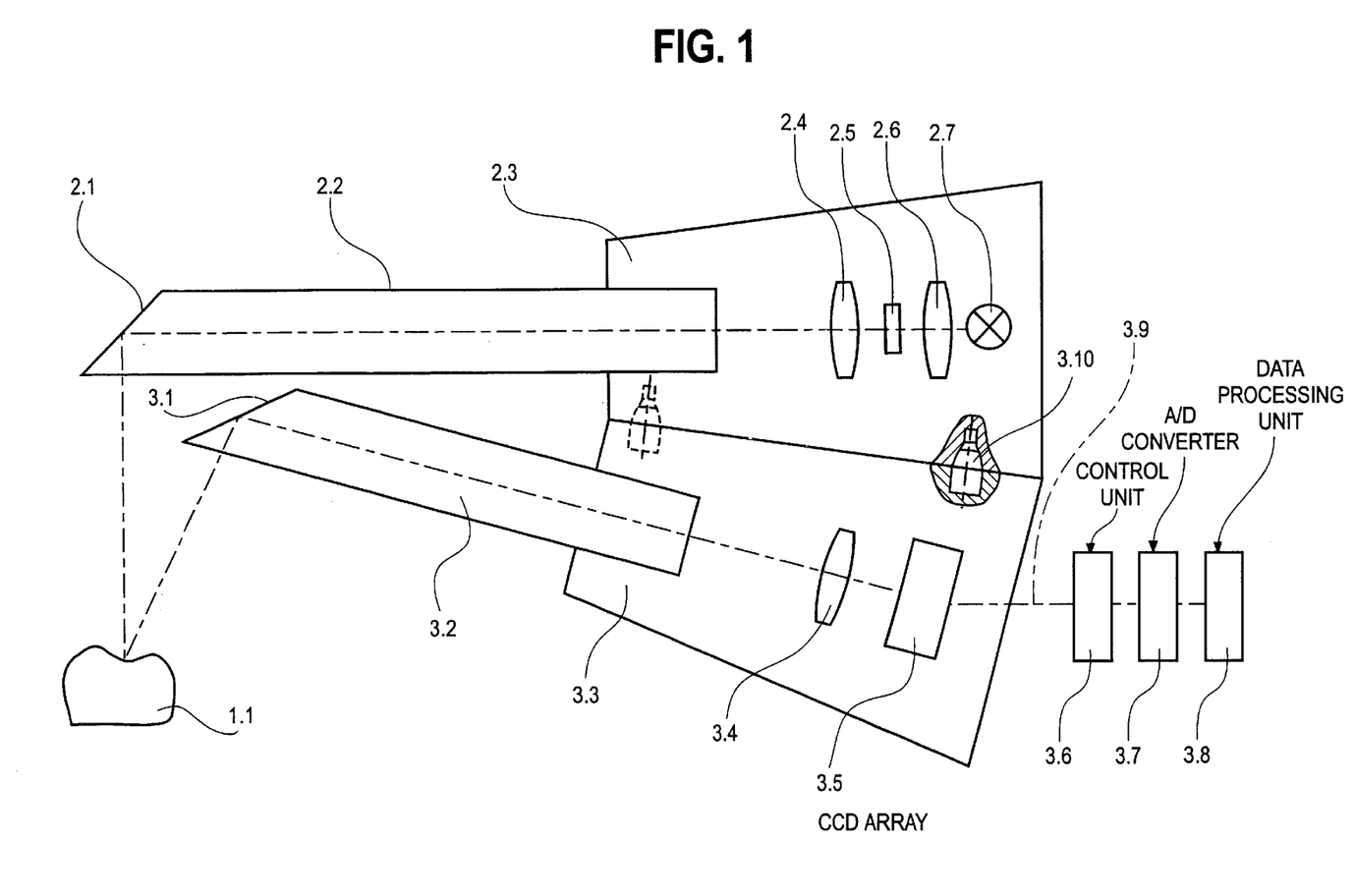
FIG. 1: In schematic form, one form of implementation of the image capture device with the projection [unit] and image capture unit separate from one another, which are here connected together, with the help of positioning rods, for the purpose of the capture of a first image under defined geometrical conditions in relation to the direction of projection and capture.
Figure 2:
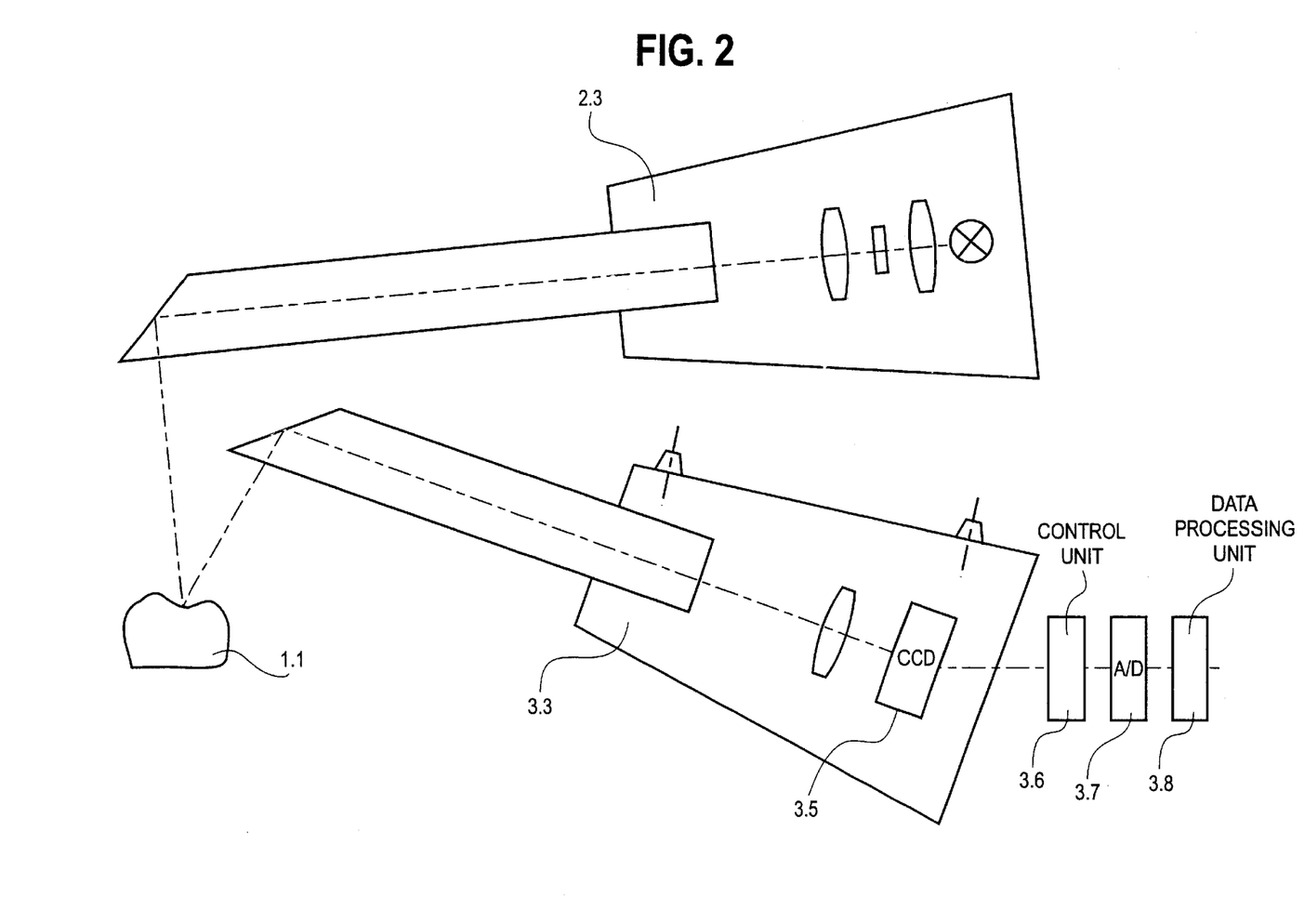
FIG. 2: The same device as in FIG. 1, but decoupled in order to carry out further captures.
Figure 3:
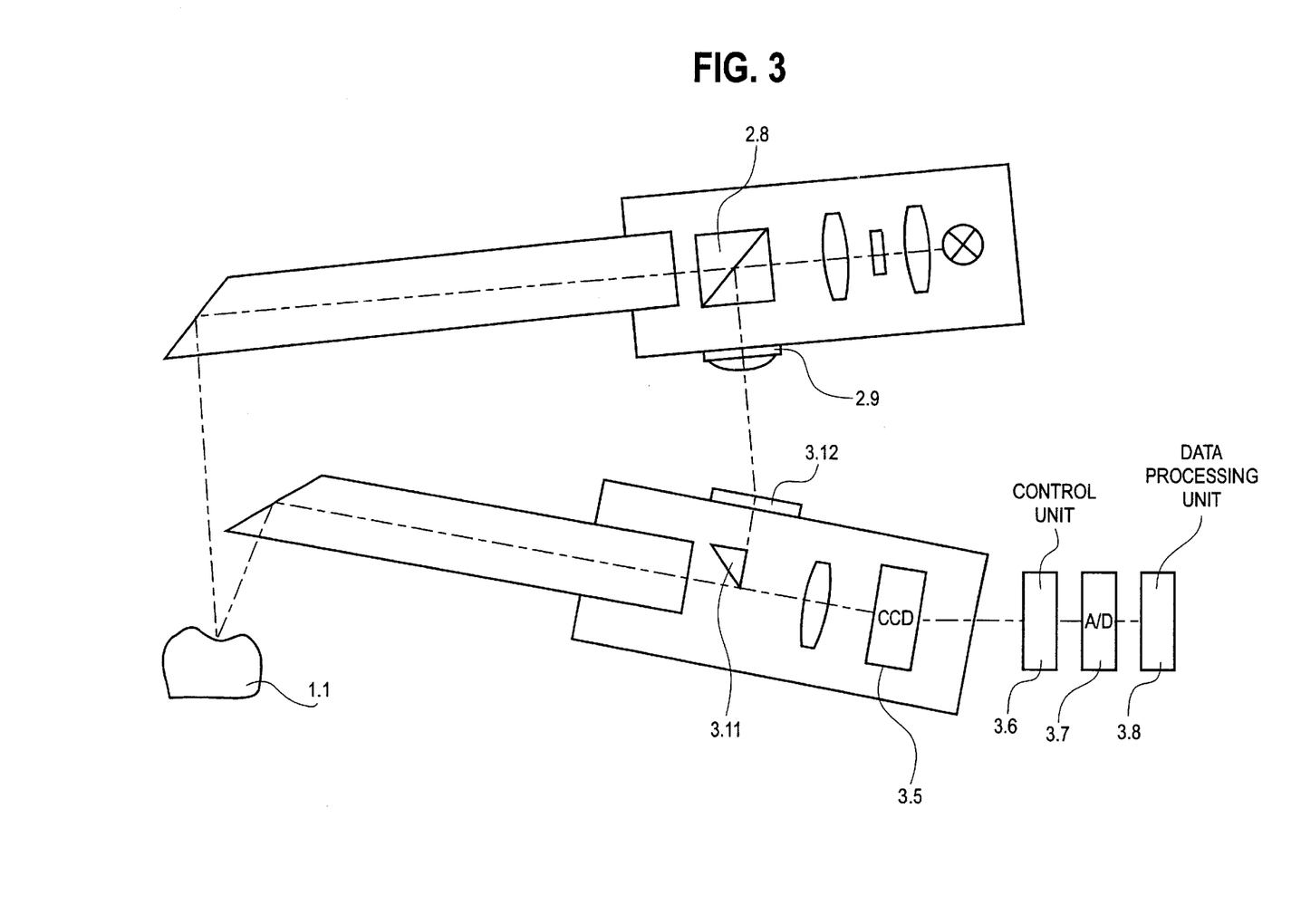
FIG. 3: In schematic form, one further form of implementation of the image capture device with the projection [unit] and image capture unit separated from one another, characterized by the additional projection of the same pattern by way of a second beam path of the projection unit directly onto a ground glass disk of the image capture unit, with this being for the purpose of the continuous calculation of their geometrical situation to one another.

In the forms of implementation in accordance with FIGS. 1, 2 and 3, the projection unit and the image capture unit are, for the purpose of simplifying the description, only depicted schematically without known, obvious device parts. For the simplification of the description, it was additionally dispensed with describing forms of implementation of device parts that belong to the state of the art, such as specific forms of implementation of connections or of part-fixing devices, in full detail.

In the form of implementation of FIG. 1, the source of beams (2.7), the optical devices (2.4 and 2.6), and the pattern support (2.5) are rigidly connected with the support mount (2.3) of the projection unit. The optical devices in the form of implementation depicted here involve a source of beams (2.7) by means of which the object can be illumined on its surface, a condenser (2.6), as well as a pattern support on which the pattern (whether etched in or in the form of a slide transparency) is positioned. The support (2.2) is, for hygienic reasons (for the purpose of disinfection), connected with the support mount (2.3) in a detachable manner. The connection of the support (2.2) with the support mount (2.3) is configured in such a manner that, after a change of the support (2.2), its set geometrical positions are reproduced precisely (without adjustment). The pattern placed on the pattern support (2.5) is projected onto the object that is to be captured (1.1) by means of a beam deflection device (2.1). In order to obtain relevant information for the 3D calculation, a projected line pattern is applied transversely to the level spread on the triangulation angle.

The following are rigidly connected with the support mount (3.3) of the image capture unit: the optical device (3.4), the electronic image converter (3.5), as well as the positioning rods (3.10). The support (3.2) is, for hygienic reasons (for the purpose of disinfection), connected with the support mount (3.3) in a detachable manner. The connection of the support (3.2) with the support mount (3.3) is configured in such a manner that, after a change of the supports (3.2), its set geometrical position is reproduced precisely (without adjustment). The electronic image converter (3.5) is configured as a CCD array and connected, by way of the electrical connections (3.9), with the control unit (3.6), the A/D converter (3.7), and the data processing unit (3.8). The beams reflected from the object (1.1) are imaged on the image converter (3.5) by means of the optical devices (3.4), in this case an objective lens.

For the carrying out of the first capture, the projection unit and the image capture unit are, with the help of two positioning rods (3.10), brought into a defined position in relation to one another. The triangulation angle which is consequently known permits the calculation of 3D coordinates of the captured image.

FIG. 2 depicts the same projection unit and image capture unit, but in the decoupled condition after the carrying out of the first capture in a series of captures of the same object, however. Further images of additional areas of the object and/or from a changed direction of view can now be captured. Because of the high frequency of capture, such as of 50 Hz in the configuration depicted, for example, a high level of overlapping of the images, which is in every case sufficient, can be assumed, which makes it possible, by means of suitable registration algorithms and numerical processes, to compute the positions of the projection unit and the image capture unit relative to one another as well to the object, which positions have changed in relation to the specifically preceding capture, and to thereby also compute the triangulation angle which is specifically relevant, for example. This makes possible the determination of the 3D coordinates of an object, which could not be determined with a single capture.

FIG. 3 depicts one form of implementation in which, by means of the projection of the same pattern by way of a second beam path—that is, in addition to the (invasive) parts of the device that are used—which is guided from the projection unit to the image capture unit, the relative positions of the projection unit and of the image capture image to one another are known at the point in time of every capture. In this form of implementation, the pattern is diverted by 90 degrees by means of a beam splitting device (2.8) and projected, through a lens (2.9) with a divergent beam path positioned on the projection unit, onto a ground glass disk (3.12) positioned on the image capture unit. The image of the portion of a pattern which thereby results is, by means of a beam deflection device (3.1 1), diverted by 90 degrees into the beam path of the support of the image capture unit in such a manner that it is imaged on one half of the two-dimensional field of view of the electronic image converter (3.5). Through the evaluation of the significant pattern segments of the image in the data processing unit (3.8) by means of suitable numerical processes, the position of the projection unit relative to the image capture unit is known for every individual capture. With this form of implementation, the 3D coordinates of which can only be computed through the evaluation of a multiplicity of captures, the attainable precision of the 3D coordinates can be significantly increased in relation to the one described above, particularly in the case of complex objects.

Figure 4:
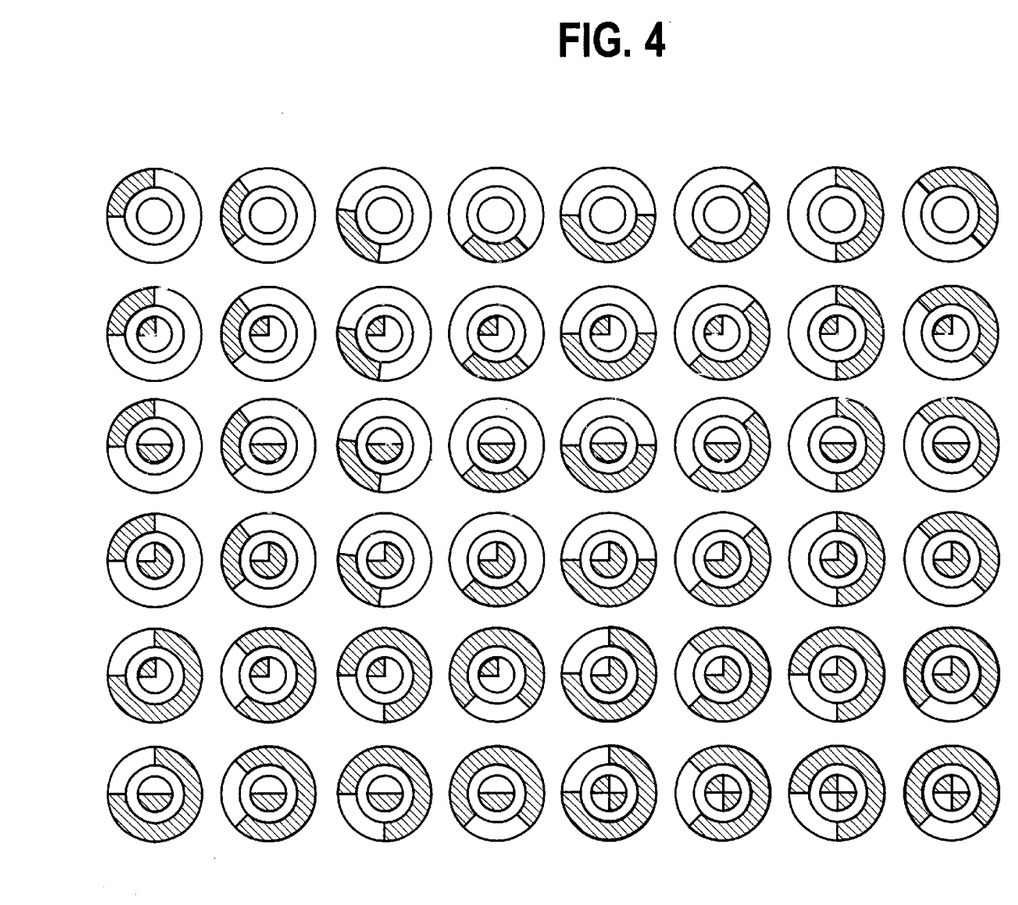
FIG. 4: By way of example, one form of implementation of a coded pattern.

FIG. 4 depicts, by way of example, one form of implementation of the pattern, through which, because of the different pattern of each of the individual concentric elements (coding), differences in the calculation of triangulation can be avoided.

One particularly advantageous use of the invention is to be seen in the area of invasive medicine. For the three-dimensional optical imaging of an organ inside the human body, for example, the forward part of the support (2.3) as well as of the support (3.2), for example, are inserted through the abdominal wall, the capture process is started by means of an activation element which is not depicted in the diagrams but which is present in the framework of the data processing unit (3.8), and, during the course of the capturing process, the projection unit and the image capture unit are moved in such a manner that all relevant surface areas of the object (1.1) are gradually represented, both on the image converter (3.5) as well as by the projection of the pattern of lines. The capture process is ended by an additional activation of the activation element stated in the preceding.

As the result of the individual image information captured, the images of the pattern of lines distorted by the surface form of the object (1.1) are now presented. Given a knowledge of the optical beam paths, and with consideration to the geometrical configuration of the projected pattern of lines for the corresponding individual exposures, a multiplicity of support points of 3D coordinates can be computed from the distortion of the pattern of lines. As the result of the 3D coordinates assigned to the individual images, furthermore, the 3D coordinates can be combined in the way and manner described above so that, as the result, the 3D coordinates of the entire surface investigated are present despite the limitation of the projection surface and of the field of view of the image capture unit. Gaps in information for reason of undercuts are thereby no longer present. The user can additionally optimize the guiding of the capture device by means of an online calculation and indication of the specific interim findings.

The forms of implementation which have been depicted here are distinguished, among other points, by the fact that:
a) No movable parts are used in the projection unit and image capture unit;
b) The optical structure is configured in a simple manner;
d) Apart from the support units (2.2 and 3.2), the support mounts (2.3 and 3.3), and the pattern support for the projection of the pattern (2.5), hardware components of the commercially available type can be used.

A process and a device in which optical devices synchronized with the image alternation frequency of the image converter, in such a manner that a pattern is alternately projected onto the surface to be measured and the surface considered is completely illuminated, is already known from the German patent application number 196 35 354.3 of the same applicant.

In one particularly advantageous configuration of the image capture device in accordance with the invention, additional devices in the previous sense are positioned and placed in such a manner that both 3D information as well as colored views of the surface scanned, for example, can be obtained from a series of individual images.

LISTING OF REFERENCE NUMBERS 1.1 Object with three-dimensional extension
2. Projection Unit 2.1 Beam deflection device (mirror)
2.2 Support (constructed here as a body of optical glass)
2.3 Support mount
2.4 Optical device (objective lens)
2.5 Pattern support (with pattern etched in or a slide transparency, for example)
2.6 Optical device (condenser)
2.7 Source of beams
2.8 Beam splitting device
2.9 Optical device (lens)
3. Image Capture Unit
3.1 Beam deflecting device (mirror)
3.2 Support (constructed here as a body of optical glass)
3.3 Support mount
3.4 Optical device (objective lens)
3.5 Electronic image converter (CCD Array)
3.6 Control unit
3.7 A/D converter-frame Grabber
3.8 Data processing unit
3.9 Electrical connections
3.10 Positioning rods
3.11 Beam deflecting device (deflecting prism)
3.12 Ground glass disk

What is claimed is:

1. Method for acquiring data as to the shape of an object comprising the steps of:
   projecting a pattern using a projection device onto said object;
   performing an optical pick up of a scattering of said pattern from said object using an image pick up; wherein
   during operation of said steps of projecting and performing an optical pick up, (1) the projection device is spatially separated from the image pick up, and (2) the projection device is uncoupled from and moveable with respect to the image pick up; and
   determining the geometrical arrangement of said image pick up and said projection device during or after said steps of projecting and performing an optical pick up.

2. Method according to claim 1, characterized in that the step of determining the geometrical arrangement includes determining the geometrical arrangement using a measuring means.

3. Method according to claim 2, wherein said measuring means comprises an optical measuring means.

4. Method according to claim 3, characterized in that the step of determining the geometrical arrangement includes using triangulation calculations as part of the optical measuring means.

5. Method according to claim 4, characterized in that the step of projecting the pattern includes splitting said pattern with a beam splitter and thereby projecting a pattern onto an object being surveyed, and onto a surface rigidly connected to the image pick up and having a known spatial extent.

6. Method according to claim 5, further including the step of imaging the pattern projected onto said surface with said image pick up using an optical element.

7. Method according to claim 5, wherein said surface comprises a ground glass disk.

8. Method according to claim 6, wherein said optical element comprises a mirror.

9. Method according to claim 6, wherein the step of projecting the pattern further includes:
   projecting the pattern along two optical axes; preparing at least two single images as part of the pattern; and
   switching an optical device alternatively between transparent and opaque states in synchronization with respect to an image refresh rate.

10. Method according to claim 1:
    wherein during the step of performing an optical pickup a first image and a second image are received, and the geometrical arrangement of the projection device relative to the image pick up is known for the first image and unknown for the second image due to movement of the image pickup and/or the projection device relative to each other, and the method further comprising the steps of
    forming a plurality of 3D coordinates of a 3D surface of the object from the first image, wherein there is an overlap of image data in the first and second images, and
    determining the geometrical arrangement of the projection device to the image pick up for the second image.

11. Method according to claim 10, wherein the step of determining the geometrical arrangement further includes using an optimizing evolution strategy.

12. The method of claim 10, wherein said step of determining further comprises the step of computing a plurality of possible 3D surfaces based on assumptions as to movement of said projection device and/or said image pickup and selecting the surface which matches most closely to said 3D surface.

13. Device for acquiring data as to the shape of an object comprising:
    a projection device projecting a pattern onto a surface of said object; and
    an optical image pick up having an electronic image converter, wherein the projection device is spatially separated from the image pick up, and the projection device is moveable with respect to and uncoupled from the image pick up during the acquiring of data.

14. Device according to claim 13, wherein the image pick up is initially coupled in a rigid manner relative to the projection device, wherein the orientation of the projection device is known relative to the image pick up.

15. The device of claim 13, wherein the image pick up generates a first and a second image while said projection device and image pick up are moveable and uncoupled with respect to each other, and wherein the device further comprises a data processing unit forming a plurality of 3D coordinates of a 3D surface of the object from said first image and wherein there is an overlap of image data in the first and second images, and
    wherein said data processing unit determines the geometrical arrangement of the projection device relative to the image pick up for the second image.

16. The device of claim 15, wherein the data processing unit computes a plurality of possible 3D surfaces based on assumptions as to movement of said projection device and/or said image pickup and selecting the surface which matches most closely to said 3D surface.

17. A method for acquiring data as to the shape of an object comprising the steps of:
    receiving at a pick-up device a first image representing a surveyed object while a projection device has a first orientation with respect to the pick-up device, wherein the first orientation is known, and the first image is based upon a pattern projected by the projection device; and
    receiving a second image representing the surveyed object at the pick-up device while the projection device has a second orientation with respect to the pick-up device and object, wherein the second orientation is different than the first orientation due to an uncoupling of said projection device and said pick up device during operation of said pick up device and said projection device, and the second image is based upon the pattern projected by the projection device.

18. The method of claim 17 further comprising the steps of:

generating a first three-dimensional image based upon the first image;

generating a second three-dimensional image based upon the second image.

19. The method of claim 18 wherein the second three-dimensional image is generated by determining the second orientation in all degrees of freedom.

20. The method of claim 19 further comprising the step of:

determining the second orientation in all degrees of freedom based upon an overlap between the first image and the second image.

21. The method of claim 20, wherein determining the second orientation includes generating at least one estimated three-dimensional image based upon the second image.

22. The method of claim 21 wherein generating the estimated three-dimensional image(s) includes the steps of:

calculating a three-dimensional image based upon the second image and an estimated second orientation;

determining a best fit orientation between the first three-dimensional image and the estimated three-dimensional image; and determining a grade of the fit.

23. The method of claim 22, wherein the estimated second orientation is based upon the first orientation.

24. The method of claim 22, wherein the estimated second orientation is based upon data not reflected from a surface of the surveyed object.

25. The method of claim 22 further comprising the steps of:

splitting said pattern with a beam splitter and thereby projecting said pattern onto an object being surveyed, and onto a surface connected to the image pick up means and having a known spatial extent, using a plurality of estimated second orientations until a predefined grade of fit is reached; and selecting the second orientation that provides the best grade of fit.

26. A system for acquiring data of a surface of an object comprising:

a projection device having a first beam carrier to project a pattern away from said projection device;

an image pick-up device for detecting scattering of said projected pattern from said object; and means for deriving a relative orientation between the image pick-up device and the projection device;

wherein during operation of said system aid image pickup and said projection device are uncoupled from each other and freely moveable relative to each other.

27. The system of claim 26, further comprising first and second alignment features which, when engaged to each other, provide a known orientation between said projection device and said image pickup device.

28. The system of claim 26, wherein said means for deriving comprises a surface (3.12) coupled to said image pick-up device and wherein said projection pattern impinges on said surface and is imaged by said image pick-up device.

29. The system of claim 26, wherein said means for deriving comprises a data processing unit.

* * * * *